United States Patent
Zucker et al.

(10) Patent No.: US 8,783,298 B2
(45) Date of Patent: Jul. 22, 2014

(54) BREATHING HOSE

(75) Inventors: Shlomo Zucker, Michmoret (IL); Menachem Dvir, Herzelia (IL)

(73) Assignee: Kast Silicone Ltd., Kibbutz Kiryat Anavim (IL)

( * ) Notice: Subject to any disclaimer, the term of this patent is extended or adjusted under 35 U.S.C. 154(b) by 651 days.

(21) Appl. No.: 12/511,121

(22) Filed: Jul. 29, 2009

(65) Prior Publication Data
US 2011/0023987 A1 Feb. 3, 2011

(51) Int. Cl.
*F16L 11/00* (2006.01)

(52) U.S. Cl.
USPC .......................................... 138/120; 138/155

(58) Field of Classification Search
USPC .................... 138/120, 155; 405/43, 45, 47
See application file for complete search history.

(56) References Cited

U.S. PATENT DOCUMENTS

| | | | |
|---|---|---|---|
| 3,465,529 A * | 9/1969 | Helle | 405/47 |
| 3,552,778 A | 1/1971 | Muller | |
| 3,939,875 A | 2/1976 | Osborn et al. | |
| 4,001,054 A * | 1/1977 | Makepeace | 148/220 |
| 4,567,916 A | 2/1986 | Antal et al. | |
| 4,753,554 A * | 6/1988 | Jeter | 405/224.2 |
| 4,824,287 A * | 4/1989 | Tracy | 405/36 |
| 4,927,191 A | 5/1990 | Mikol | |
| 5,062,420 A | 11/1991 | Levine | |
| 5,284,134 A | 2/1994 | Vaughn et al. | |
| 5,477,852 A | 12/1995 | Landis et al. | |
| 5,501,212 A | 3/1996 | Psaros | |
| 5,572,994 A | 11/1996 | Smith | |
| 5,639,364 A * | 6/1997 | Houck et al. | 210/170.01 |
| 5,682,924 A * | 11/1997 | Powell | 138/109 |
| 5,816,742 A | 10/1998 | Cordewener | |
| 6,199,592 B1 * | 3/2001 | Siferd et al. | 138/109 |
| 6,398,266 B1 | 6/2002 | Crump | |
| 6,415,789 B1 | 7/2002 | Freitas et al. | |
| 7,384,212 B2 * | 6/2008 | Currivan | 405/43 |
| 7,886,774 B1 * | 2/2011 | Popp | 138/121 |
| 2001/0017164 A1* | 8/2001 | Fukui et al. | 138/125 |
| 2002/0091300 A1* | 7/2002 | Peng et al. | 600/37 |
| 2003/0070680 A1 | 4/2003 | Smith et al. | |
| 2004/0035419 A1 | 2/2004 | Serowski et al. | |
| 2004/0244858 A1* | 12/2004 | Jeong | 138/122 |
| 2005/0077726 A1 | 4/2005 | White et al. | |

(Continued)

FOREIGN PATENT DOCUMENTS

| | | |
|---|---|---|
| DE | 202005002576 | 6/2005 |
| EP | 1138340 | 12/2004 |
| GB | 851993 | 10/1960 |
| WO | WO 2009/022004 | 2/2009 |

*Primary Examiner* — James Hook
(74) *Attorney, Agent, or Firm* — Daniel J. Swirsky; AlphaPatent Associates Ltd.

(57) ABSTRACT

A hose formed by a plurality of subunits in tandem arrangement particularly useful for use in a breathing apparatus. Each of the subunits comprises a plurality of repeat subunits in tandem arrangement, each of said subunits comprising: a proximal subunit-to-subunit connector member at a proximal end of each subunit; a distal subunit-to-subunit connector member at a distal end of each subunit; at least one interlocking ring; and at least one gas and/or moisture-permeable member disposed intermediate and connected to the at least one interlocking ring and one or both of the proximal and distal subunit-to-subunit connector members. In other embodiments, the member intermediate the interlocking ring and subunit-to-subunit connector members is a non-rigid member, and more particularly has a frusto-conical shape.

7 Claims, 4 Drawing Sheets

(56) References Cited

U.S. PATENT DOCUMENTS

| | | |
|---|---|---|
| 2007/0163600 A1 | 7/2007 | Hoffman |
| 2007/0215147 A1 | 9/2007 | Ho |
| 2007/0246043 A1 | 10/2007 | Kwok et al. |
| 2007/0277828 A1 | 12/2007 | Ho et al. |
| 2009/0025724 A1 | 1/2009 | Herron, Jr. |
| 2009/0250924 A1 | 10/2009 | Tisbo et al. |
| 2009/0321105 A1* | 12/2009 | Sawyer .......................... 174/69 |
| 2010/0083965 A1 | 4/2010 | Virr et al. |
| 2010/0126616 A1* | 5/2010 | Kanao .......................... 138/122 |

\* cited by examiner

BREATHING HOSE

FIELD OF THE INVENTION

The present invention relates a hose or conduit, in particular a hose or conduit implementable in a medical or healthcare device, especially useful for a breathing apparatus.

BACKGROUND ART

Continuous positive airway pressure (CPAP) systems typically use flexible plastic tubing or hose, for example of polyethylene or polypropylene, for conveying gases such as air or oxygen to a patient.

U.S. Pat. No. 7,472,707 (Wood et al.) includes a disclosure of a ribbed air delivery hose, with a round or oval profile, designed so that the hose's cross-sectional area does not change when the hose is bent (e.g. around a patient's ear).

Regardless, it remains an issue that a CPAP mask or cannula (e.g. an apnea cannula fitted in a nare or nares) can be pulled into undesirable positions by movement of the patient resulting in loss of the seal or removal or partial removal of the mask/cannula. If there is a loss of the seal, the CPAP system may sense a loss of air/oxygen delivery and respond by increasing flow, which is inefficient and may be noisy. Condensation in the tubing/hose is another common issue. The desire to mitigate pulling on a nasal continuous positive airway pressure (NCPAP) breathing interface device (e.g. mask or cannula) is particularly important in the case of such a device that does not include a retention strap, which may be uncomfortable and inconvenient to adjust.

In this regard, US 2009/078259 (Koolj et al.) discloses a breathing tube that is extensible and retractable via a configuration similar to a flexible drinking straw to accommodate movement of the patient, for example movement of the patient's head. The extensible/retractable tube may be attached to a patient interface using a swivel elbow assembly. The retractable tube may be of sufficient length to accommodate some movement of the patient's head without extension or retraction of the tube.

SUMMARY OF THE INVENTION

The present invention relates to a hose particularly useful for delivering air, oxygen or other gas or gases to a breathing apparatus such as a nasal ventilation interface device. Via the hose of the present invention, air or other gas(es) is directed into the nasal interface device and thence into the nasal passages. The hose of the present invention can be beneficially implemented with forced breathing or forced airway ventilation nasal systems, such as a continuous positive airway pressure (CPAP) system.

It should be understood however, that the present hose may have other medical applications as well as non-medical applications.

It is a particular feature of the present hose that it contains a portion or portions comprising a non-rigid member (e.g. a flexible fabric-like member) providing the hose with multiple degrees of freedom of movement.

It is a particular feature of the present hose that it contains a portion or portions comprising a gas and/or liquid permeable material (e.g. via the afore-mentioned non-rigid member (e.g. fabric-like member) and in particular permeable material portions among which at least some are gas permeable and some are liquid permeable to facilitate the diffusion of moisture and/or gases such as carbon dioxide from the hose.

It is another particular feature of the present hose that it contains a portion or portions comprising rigid or semi-rigid members to help prevent loss of cross section area, which might affect gas flow.

It is another particular feature of the present hose that it is designed to allow swiveling of components thereof relative to each other.

It is another particular feature of the present hose that it is designed to allow a slight twisting motion.

It is another particular feature of the present hose that it is designed to allow a change in length thereof, both elongation and compression.

Accordingly, the present invention provides a hose comprising: a plurality of repeat subunits in tandem arrangement, each of said subunits comprising: a proximal subunit-to-subunit connector member at a proximal end of each subunit; a distal subunit-to-subunit connector member at a distal end of each subunit; at least one interlocking ring; and at least one gas and/or moisture-permeable member disposed intermediate and connected to the at least one interlocking ring and one or both of the proximal and distal subunit-to-subunit connector members.

According to some embodiments, the hose comprises at least one gas and/or moisture-permeable member with a frusto-conical shape. In some embodiments, at least one of the subunit-to-subunit connector members comprises an end member and a fabric to end-member connector ring connected to each other and adapted to swivel with respect to each other. In some embodiments, each subunit comprises two fabric members and one interlocking ring. In some embodiments, the permeable members comprise an axial flange sized to snugly fit on the subunit-to-subunit connectors. In some embodiments, the permeable members comprise an axial flange sized to snugly fit on the fabric to end-member connector ring. In some embodiments, at least one of the interlocking rings comprises two or more interlocking ring members, providing for a swivel movement therebetween. In some embodiments, the at least one permeable member comprises a synthetic woven or non-woven material providing a certain degree of permeability to liquids. In some embodiments, the at least one permeable member comprises a synthetic woven or non-woven material providing a certain degree of permeability to gases.

BRIEF DESCRIPTION OF THE DRAWINGS

The present invention, which shall be described via exemplary embodiments, will be understood and appreciated more fully from the following detailed description taken in conjunction with the appended drawings in which.

DETAILED DESCRIPTION OF SOME EMBODIMENTS OF THE INVENTION

Illustrative embodiments of the invention are described below. In the interest of clarity, not all features of an actual implementation are described. It will be appreciated that in the development of any such actual embodiment, numerous implementation-specific decisions must be made to achieve the developers' specific goals, such as compliance with system-related and business-related constraints, which vary from one implementation to another. Moreover, it will be appreciated that such a development effort might be complex and time-consuming, but would nevertheless be a routine undertaking for those of ordinary skill in the art having the benefit of this disclosure.

Figure 1:
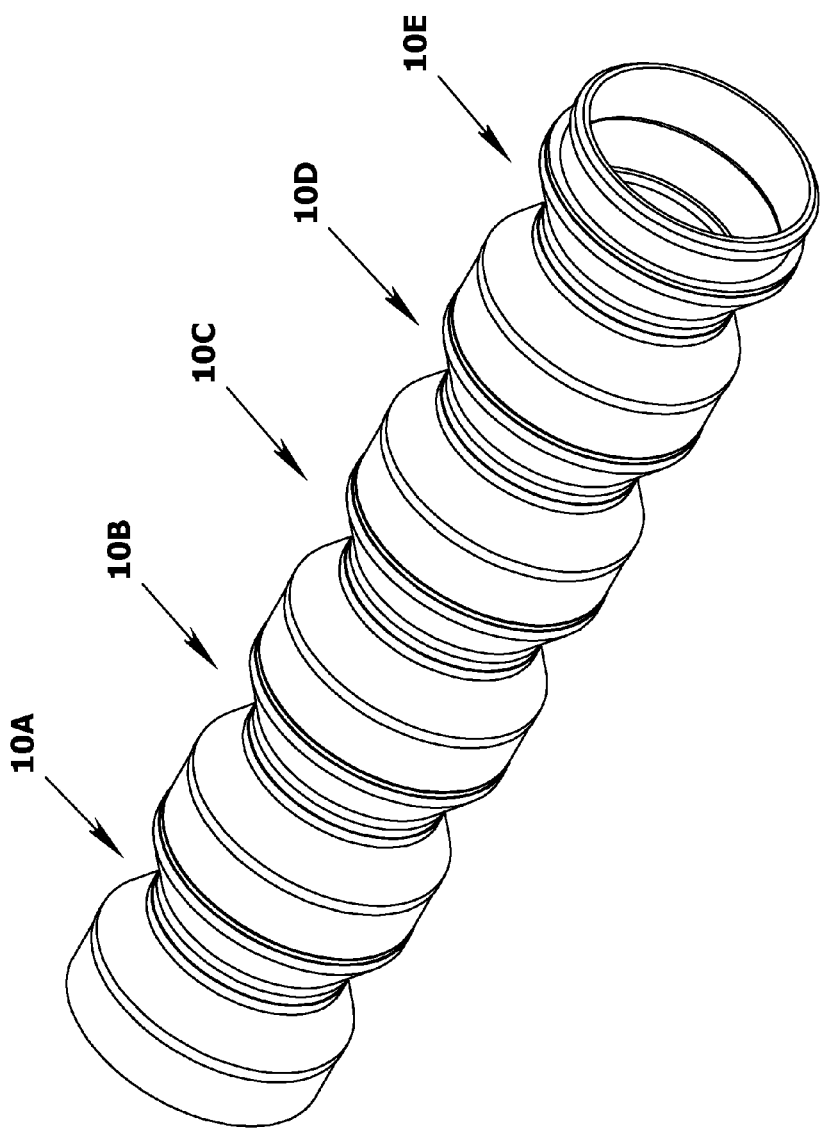
FIG. 1 is an isometric view of an embodiment of a hose of the present invention.

The figures show embodiments of a hose of the present invention comprising a plurality of repeat subunits 10, for example five such subunits labeled 10A-10B in FIG. 1. The subunits 10 are connected in series to form the hose. Although the subunits 10 are illustrated as identical or repeat units, according to other embodiments (not shown) the subunits can have "heterogeneous" designs, including containing a swiveling elbow (not shown) or the like.

Figure 2:
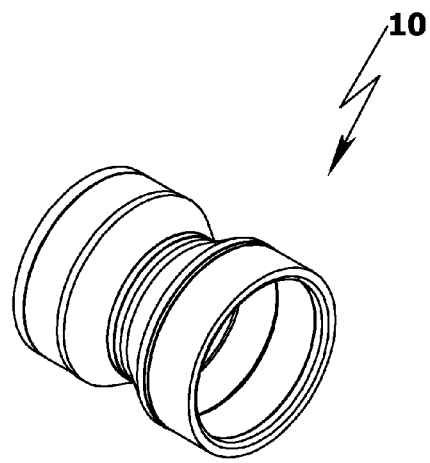
FIG. 2 is an isometric view of a single subunit of the hose of FIG. 1.
Figure 3:
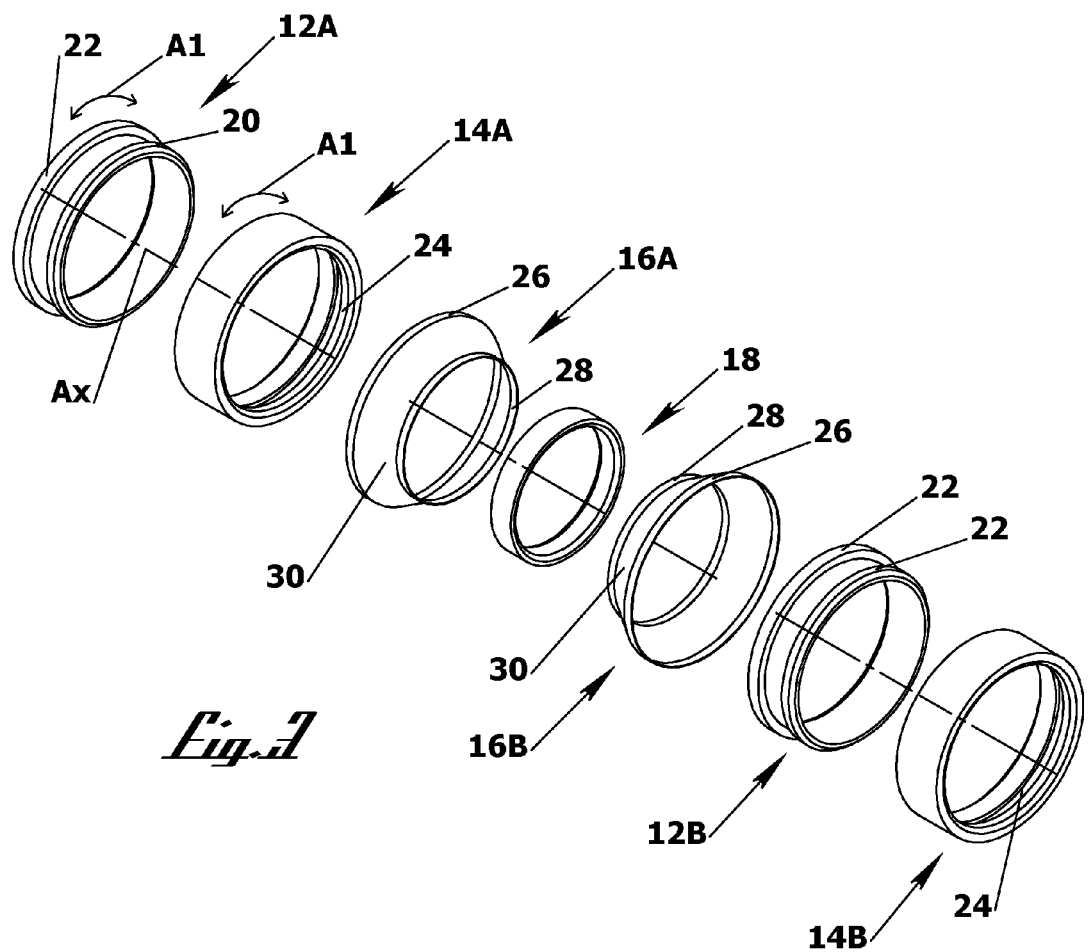
FIG. 3 is an exploded isometric view of the subunit of FIG. 2.

FIGS. 2 and 3 show a single subunit 10 in a perspective and an exploded perspective views, respectively. Subunit 10 comprises a first annular end member 12A, a first fabric to end-member connector ring 14A, a first gas and/or liquid permeable member for example a fabric member 16A, a fabric member to fabric member interlocking ring 18, a second fabric member 16B, a second fabric to end-member connector ring 14B and a second annular end member 12B.

End members 12A, 12B; connector rings 14A, 14B; and interlocking ring 18 are made of a rigid or semi-rigid, medically appropriate material for example comprising an ABS copolymer, polycarbonate, polyacetal, polyamide, alloys thereof, or the like. Such materials preferably have a relatively low coefficient of friction, to allow swiveling of the rigid/semi-rigid components relative to each other. Some of the fabric members 16A, 16B are made of a liquid permeable material whereby moisture, e.g. from an exhalation of the patient, can be transferred outside the hose. Other fabric members 16A, 16B are made of a gas permeable material whereby, for example, carbon dioxide from an exhalation of the patient can be transferred outside the hose.

End members 12A and 12B comprise a distal annular shoulder 20 and a proximal annular shoulder 22. Connector rings 14A and 14B comprise an interior annular groove 24 that interlocks, for example by a snap-like connection, with annular shoulders 20 and 22 of end members 12A and 12B. Such connection facilitates both the opportunity for a clockwise or counter clockwise swiveling of end members 12A and 12B with respect to connector rings 14A and 14B about longitudinal axis Ax, as indicated by double headed arrows A1. As can be seen in FIG. 3, the positions of end member 12B and connector ring 14B are switched so that end member 12A can connect to the connector ring of a subsequent subunit 10.

Fabric members 16A and 16B typically has a frusto-conical shape, of which the major and the minor circumferences are each furnished with major axial flange 26 and minor axial flange 28, respectively and an intermediate tapered portion 30.

Figure 4:
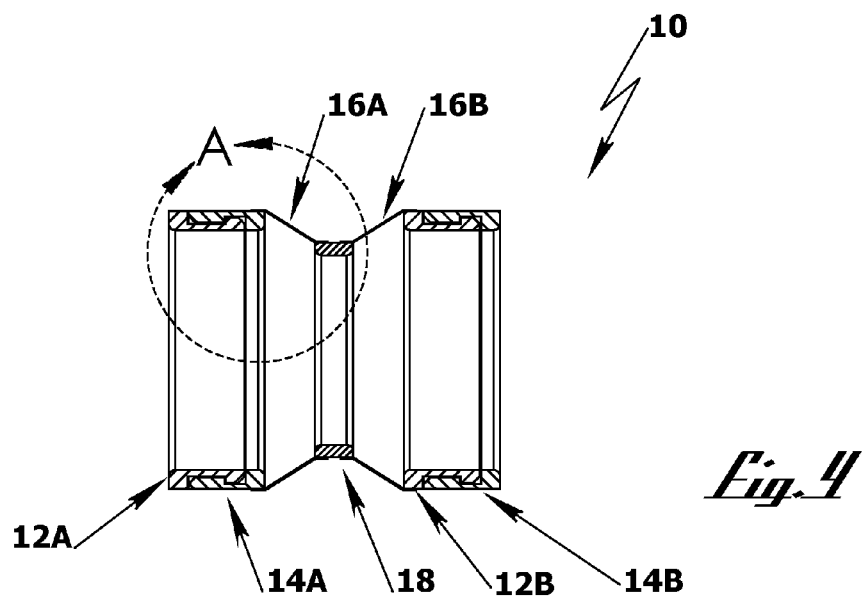
FIG. 4 is an side sectional view of the subunit of FIG. 2.
Figure 5:
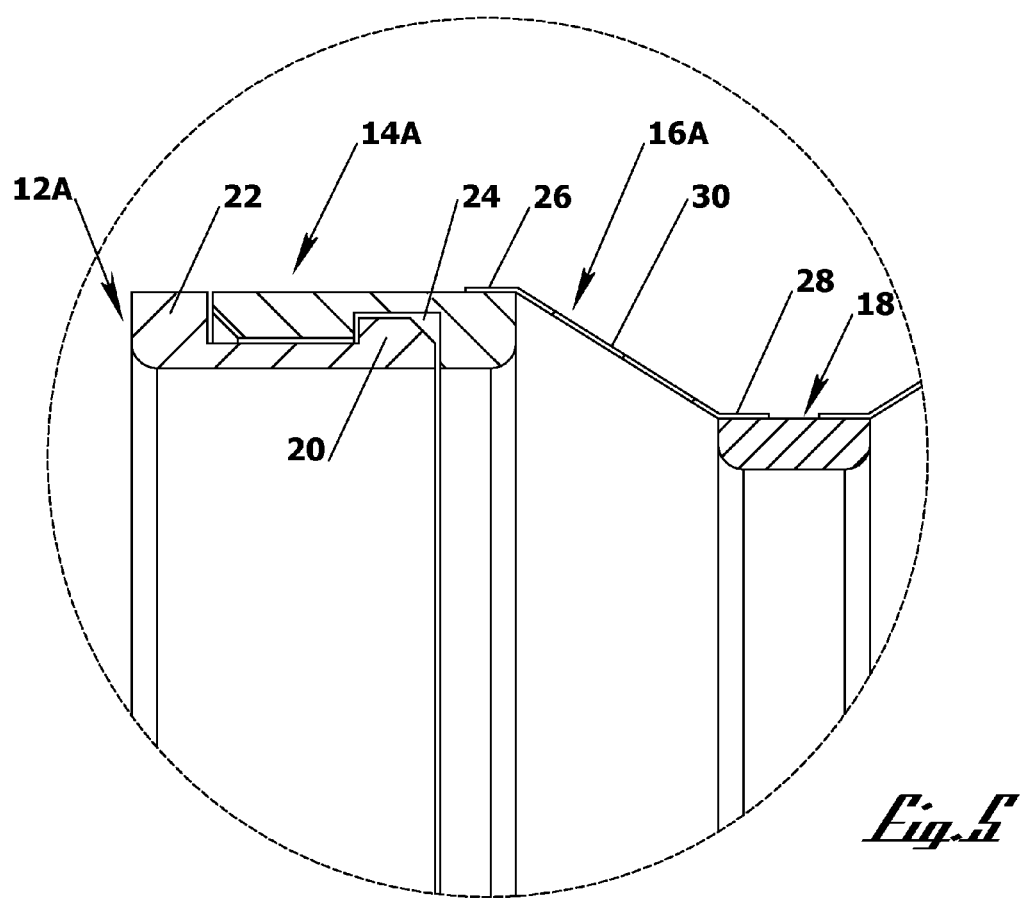
FIG. 5 is an enlarged view of area "A" of FIG. 4.
Figure 6:
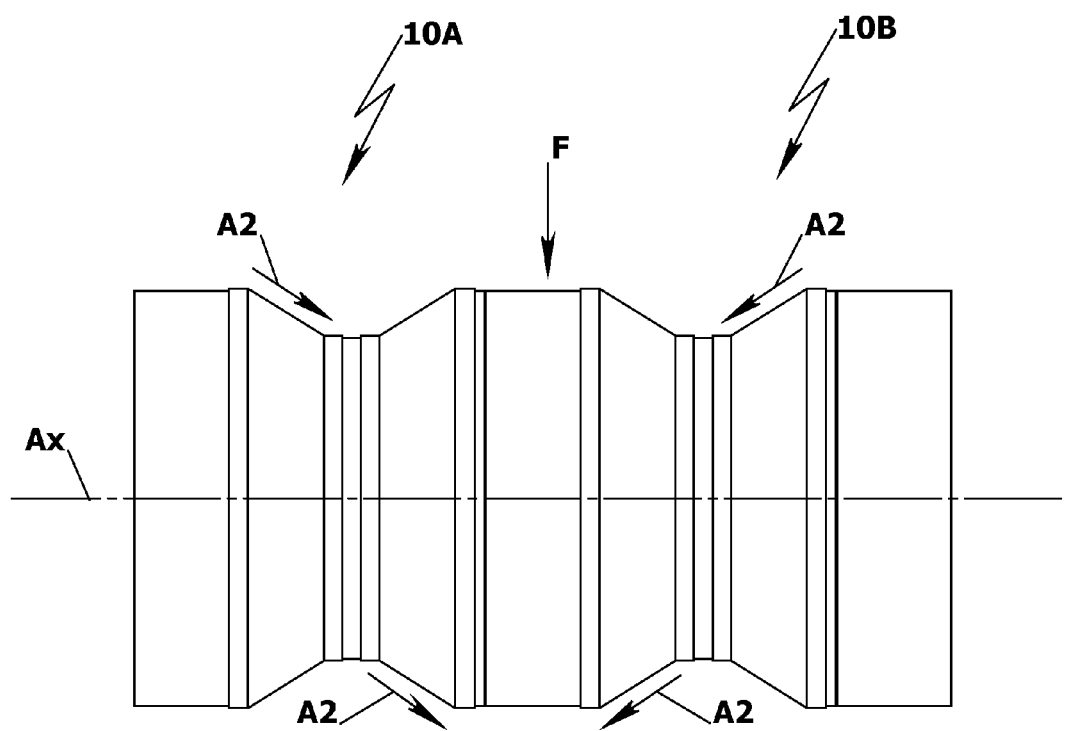
FIG. 6 is a side sectional view of two connected subunits of FIG. 2.

As illustrated best in FIGS. 4 and 5, major axial flange 26 is sized so it can snugly fit on distal annular shoulder 20 and proximal annular shoulder 22; and minor axial flange 28 is sized so it can snugly fit on interlocking ring 18. Without limitation to a particular design, it has been seen that a taper angle of about 45 degrees for intermediate tapered portion 30 tends to substantially preserve the cross-sectional area of the hose's flow opening despite the expected bending of the hose when in use, including multidirectional bending that may occur if a patient moves his or her head. In this regard, it is believed that the frusto-conical shape (i.e. angled intermediate tapered portion 30 of the fabric members 16A and 16B) provides the resistance to loss of cross-sectional flow area upon bending thereof or a force (e.g. a perpendicular force F) upon the hose via tension on the fabric members as illustrated by arrows A2.

Minor axial flange 28 at fabric member's minor circumference is sized in diameter and width so it can snugly fit on interlocking ring 18. In accordance with some embodiments, there is a fabric member essentially composed of an integration of fabric members 16A and 16B precluding the need for interlocking ring 18. Regardless, interlocking ring 18 may prove advantageous for preserving the cross-sectional flow area of the hose during when in a bent configuration and upon movement of the hose.

In some embodiments, annular end member 12A together with connector ring 14A (and/or annular end member 12B together with connector ring 14B) of some or all subunits 10 form a monolithic or other unitary element; i.e. an end member comprising the functions of connection to the gas and/or liquid permeable member (fabric members 16A, 16B) and connection to an end member of a subsequent subunit 10. On the other hand, in some embodiments interlocking ring 18, illustrated as a unitary element, may comprise two or more members, for example analogous to end members 12A and 12B connection with connector rings 14A and 14B, and thus provide another swivel point.

The fabric members 16A and 16B, in accordance with some embodiments of the present invention, comprise a synthetic woven or non-woven textile, examples of which include polyamides/nylon. In accordance with particularly preferred embodiments, the material or textile of the fabric members 16A and 16B is characterized by a certain degree of permeability to liquids, notably moisture resulting from exhaling or humidification of gas(es) fed to the patient. In other particularly preferred embodiments, the fabric members 16A and 16B are characterized by at least a degree of permeability to gases, such as water vapor and carbon dioxide (particularly in systems where the hose serves as an outlet passageway as well as a delivery passageway). According to still other particularly preferred embodiments, the hose comprises at least some fabric members 16A and 16B that are liquid permeable and at least some fabric members that are gas permeable.

Fabric members 16A and 16B provide the hose with a number of degrees of freedom of movement. The hose can be bent in any direction; twisted; and axially compressed and elongated. In addition, the hose can swivel about longitudinal axis Ax due to turning of the end members 12A, 12B relative to connector rings 14A, 14B, respectively, about the longitudinal axis. This freedom of movement provides for a more convenient and reliable performance of the hose implemented in breathing or forced airway ventilation systems, particularly such systems that are employed during a non-sedative/ordinary sleep.

The invention claimed is:
1. A hose for delivering breathing gas, the hose comprising:
at least one non-rigid member providing the hose with multiple degrees of freedom of movement while delivering breathing gas, each said non-rigid member having a frusto-conical shape; and
at least two rigid or semi-rigid member preventing loss of cross-sectional area and at least providing a swivel movement between two of said rigid or semi-rigid members.
2. A hose according to claim 1, wherein said at least one non-rigid member is a flexible fabric-like member.

3. A hose according to claim 2, wherein said at least one non-rigid member is a permeable material.

4. A hose according to claim 1, comprising a plurality of non-rigid members and a plurality of rigid or semi-rigid members, wherein said non-rigid members and said rigid or semi-rigid members are alternately arranged along said hose.

5. A hose according to claim 1, wherein said rigid or semi-rigid members are connector rings connecting adjacent non-rigid members together.

6. A hose according to claim 1, wherein said non-rigid members include an axial flange sized to snugly fit on an adjacent rigid or semi-rigid member.

7. A hose according to claim 1, wherein said hose is gas or liquid permeable.

* * * * *